(12) United States Patent
Lin

(10) Patent No.: US 7,993,307 B2
(45) Date of Patent: Aug. 9, 2011

(54) SAFE MEDICAL SYRINGE WITH AN AUTOMATIC SLOWLY RETRACTABLE NEEDLE

(76) Inventor: Zuoqian Lin, Shitang Town (CN)

( * ) Notice: Subject to any disclaimer, the term of this patent is extended or adjusted under 35 U.S.C. 154(b) by 203 days.

(21) Appl. No.: 12/225,820

(22) PCT Filed: Apr. 2, 2007

(86) PCT No.: PCT/CN2007/001066
§ 371 (c)(1),
(2), (4) Date: Sep. 30, 2008

(87) PCT Pub. No.: WO2007/118407
PCT Pub. Date: Oct. 25, 2007

(65) Prior Publication Data
US 2009/0177166 A1 Jul. 9, 2009

(51) Int. Cl.
*A61M 5/00* (2006.01)
*A61M 5/32* (2006.01)
(52) U.S. Cl. ........................................ 604/195; 604/110
(58) Field of Classification Search .................. 604/110, 604/192–198
See application file for complete search history.

(56) References Cited

U.S. PATENT DOCUMENTS
2009/0240210 A1* 9/2009 Walton et al. ................. 604/196
* cited by examiner

*Primary Examiner* — Theodore J Stigell
*Assistant Examiner* — Imani Hayman
(74) *Attorney, Agent, or Firm* — Oliff & Berridge, PLC

(57) ABSTRACT

A needle gradually auto-retractable safety medical syringe includes a hollow barrel, a plunger provided in the barrel, a piston provided on the head of the plunger, a hub provided on the head of the barrel. The hub includes an elastic connecting hub providing with a needle and a hub sheath for fixing the elastic connecting hub, the elastic connecting hub may be disengaged with the head of the barrel and retracted with the effect of a spring after having finished the injection, a regually retractable bracket which are integrated with each other, the regually retractable bracket forms with at least two elastic supporting claws engaged to the inner wall of the pushing tube of the front end of the plunger after the injection finished, the elastic connecting hub allows the regually retractable device to retract in the barrel with the effect of the spring, and allows the needle to be drawn into the barrel.

24 Claims, 9 Drawing Sheets

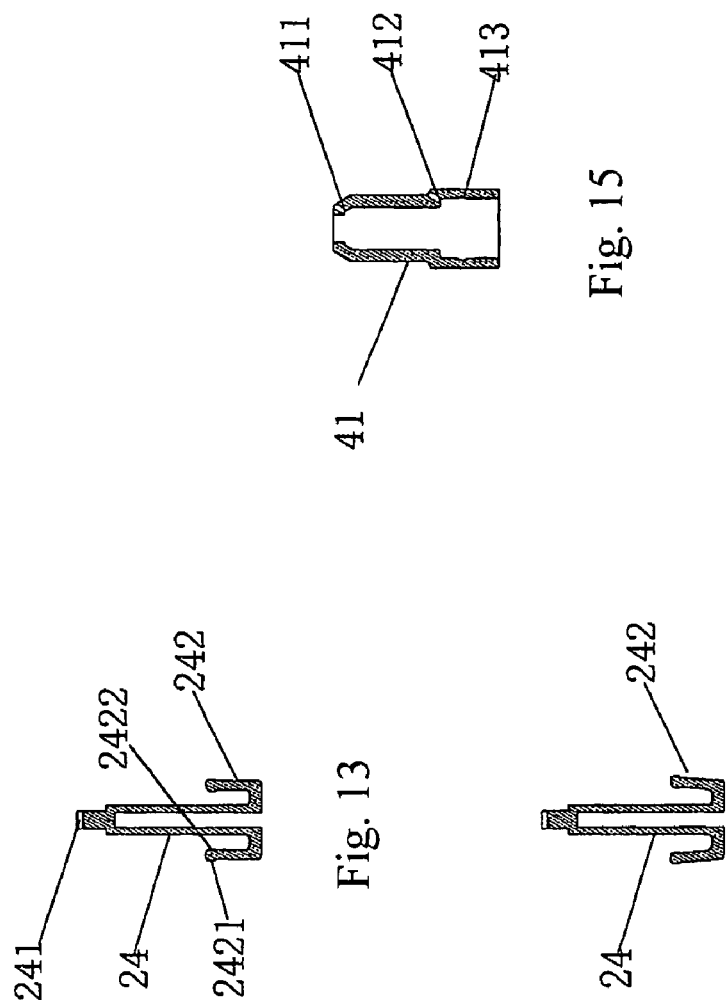
Fig. 15
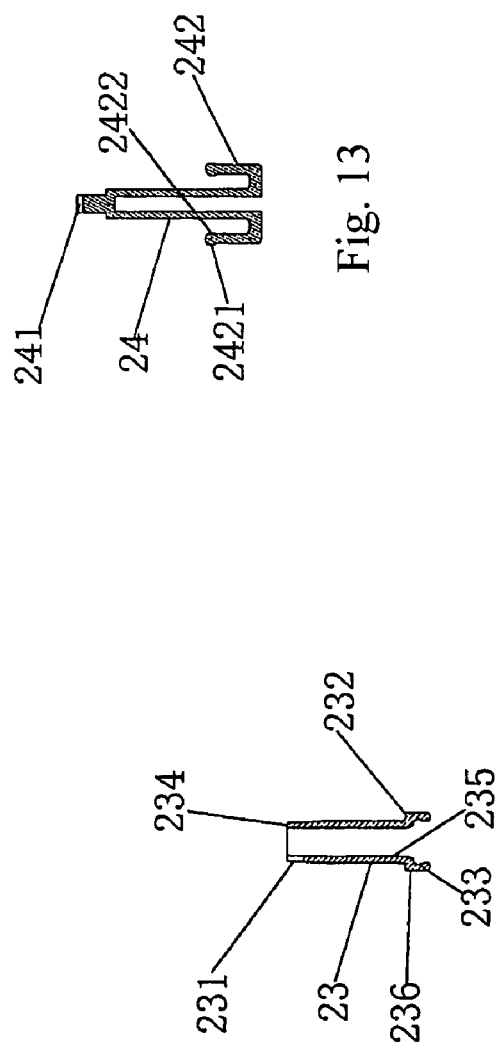
Fig. 13
Fig. 14
Fig. 12

SAFE MEDICAL SYRINGE WITH AN AUTOMATIC SLOWLY RETRACTABLE NEEDLE

TECHNICAL FIELD

The invention relates to a medical syringe, in particular, to a medical syringe with a needle which can automatically retract without the withdrawal of a doctor to hide itself after use without hurting people.

BACKGROUND ART

Modern medicine has proved that hypodermic syringes must be disposable and must be treated as medical trash after use to avoid secondary cross infection during the process of in-putting or out-taking medium for people or animals. Presently, the most commonly used disposable syringe consists of a hollow barrel, a needle, and a plunger inside the barrel. The biggest problem of this kind of syringe is that the needle of it is still exposed after use. The sharp needle makes the medical trash inconvenient for transportation or destruction Medical staffs are often hurt by the needles, which unavoidably bring secondary cross infection. Especially, the syringes used for patients with serious infectious diseases (such as AIDS, hepatitis and SARS) are great medical hidden dangers which cannot be ignored. Practices have proved that needle stick injuries caused by unsafe needles are much more than that caused by other accidents.

In recent years, as it was found that disposable syringes were taken back and used by unscrupulous persons, an auto-disposal syringe which would automatically become destroyed or locked and could not be reused, was invented at the end of last century. However, currently some syringes have serious shortcomings. Nurses have to withdraw the needle by hand after injection, which makes the injection process complicated and brings inconvenience for doctors and nurses. There is another kind of syringe, of which the needle is retracted into the cylinder under the action of spring after injection. However, the needle is retracted too fast in a sudden and blood will burst out under the body pressure from the needle hole on the body, which brings secondary cross infection.

CONTENTS OF THE INVENTION

The technical problem that this invention is going to solve is: to provide a safe medical syringe of which the needle can automatically draw back into the barrel slowly after injection. This safe medical syringe will totally solve the secondary cross infection problem of prior art.

In order to solve the above mentioned technical problems, this invention adopts the following technical scheme: a safe medical syringe with an automatic slowly retractable needle which consists of a barrel, a plunger inside the barrel, a rubber piston on the head of the plunger and a hub on the head of the barrel. The front part of the plunger is a push tube. It is characterized in that: the hub consists of an elastic connecting hub providing with a needle and a hub sheath for fixing the connecting hub; there is a spring installed between the elastic connecting hub and the hub sheath; after the injection finished, the elastic connecting hub allows the retractable device to retract in the barrel with the effect of the spring, and slows the needle to be drawn into the barrel; the front of the plunger is provided with a slow retraction device which coordinates with the elastic connecting hub in the axial direction; a backup washer and a slow retraction bracket stick together to form the slow retraction device; the slow retraction bracket consists of at least two elastic bracing claws which cooperate with the inner wall of the push tube on the front part of the plunger.

In order to solve above mentioned technical problems, this invention adopts the following technical schemes: a thru slot is provided on the top of the slow retraction bracket; an outer boss is provided on the head of the bracing claw; a boss on the upper part inside the push tube, superposing the outer boss on the head of the elastic bracing claw.

A nick slot is provided on the head of the backup washer and a protruding circle at the bottom. An inner boss is provided on the head of elastic bracing claw. The outer part of the protruding circle at the bottom of the backup washer joints with the inner boss of the elastic bracing claw.

The outside of the upper part of the backup washer cooperates closely with the piston. The outside of the middle part fits the inner hole of the push tube head movably. At the bottom, the upper surface of the boss joints with the top surface inside the push tube. An inner pocket is provided at the bottom joint with a rubber sealing ring.

An inner pocket is provided on the head of the barrel. At the bottom of the elastic connecting hub, at least two bracing claws are set symmetrically, closely jointed by clips and corresponding with the inner pocket on the head of the barrel. An inner backing pin is set in the hollow space of the elastic bracing claws as support. There are steps at the middle part inside the push tube.

This invention has the following advantages in comparison with prior art: 1. After injection, the hub cooperates with slow retraction device, and under the action of the spring, the elastic connecting hub springs the slow retraction device to retract into the barrel slowly and hides the needle inside the barrel. It solves the problem of secondary cross infection when the needle is drawn back too fast in a sudden and blood bursts out under the body pressure from the needle hole on the body; 2. The structure of the syringe is reasonable. Pushing is easy. The syringe is reliable and easy to operate. It is suitable to be applied widely.

BRIEF DESCRIPTION OF THE DRAWINGS

FIG. 12 is the cutaway view of the backup washer.

FIG. 13 is the cutaway view of the slow retraction bracket.

FIG. 14 is the cutaway view of the transfigured slow retraction bracket.

FIG. 15 is the cutaway view of the hub sheath.

MODE OF CARRYING OUT THE INVENTION

Figure 1:
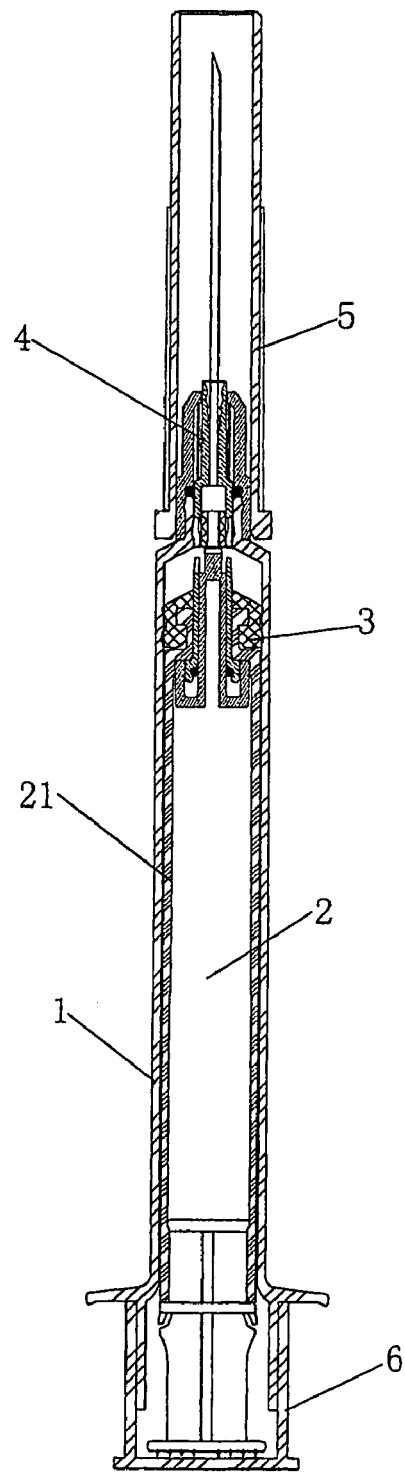
FIG. 1 is the cutaway view in the state before this invention is used.
Figure 9:
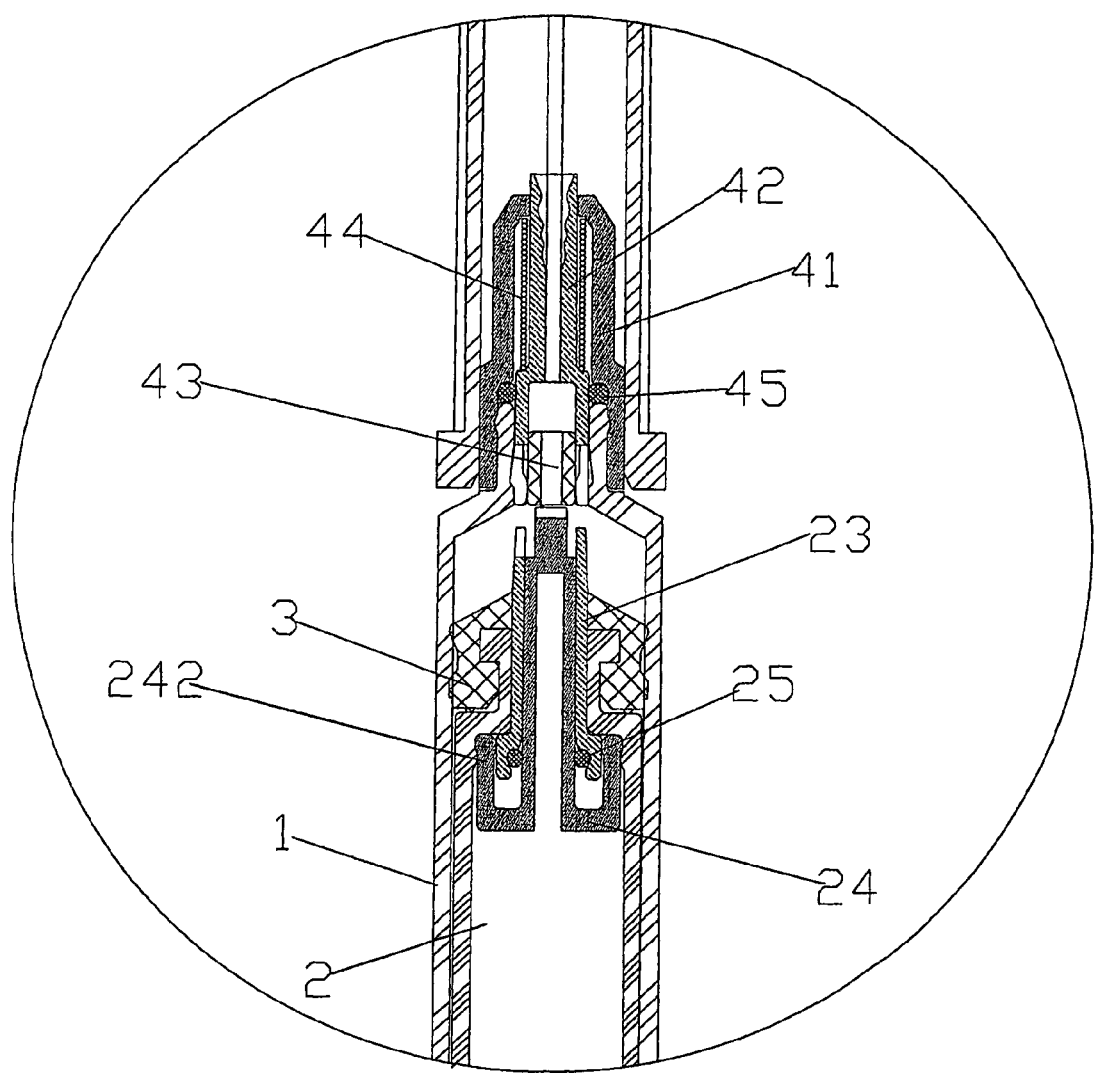
FIG. 9 is the enlarged part of FIG. 1.

It is showed in FIG. 1 that: this invention consists of a hollow barrel 1, a plunger 2 installed inside the barrel 1, a rubber plunger 3 installed on the head of plunger 2, a hub installed on the front part of the barrel 1, a push tube 21 on the front part of the plunger 2. It is showed in FIG. 9 that hub 4 consists of an elastic connecting hub 42 which is installed with an injection needle and a hub sheath 41 for fastening the elastic connecting hub 42. There is a spring 44 between the elastic connecting hub 42 and the hub sheath 41. The elastic connecting hub 42 can break away from the head of barrel 1 after pushing liquid and draw back with the action of the spring 44. On the front part of the plunger 2 is a push tube, slow retraction device is installed along the axis of the elastic connecting hub 42 and cooperates with it. The slow retraction device slowly and automatically draws the elastic connecting hub 42 back into the barrel. The slow retraction device is formed by a backup washer 23 and a slow retraction bracket 24. The backup washer 23 acts as support of the slow retraction bracket 24. There are at least two elastic bracing claws 242 cooperating with inner wall of the push tube 21 to form the slow retraction bracket 24. The bracing claw 242 with self springing action touches the inner wall of the push tube 21 and produces frictional resistance. After liquid is pushed, under the springing action of the spring 44, the elastic connecting hub 42 draws back and springs the slow retraction bracket 24 and the backup washer 23, which makes the bracing claw with springiness 242 of the slow retraction bracket 24 slide down along the inner wall of the push tube 21. The elastic connecting hub 42 and the injection needle draws back into the push tube 21. The elastic connecting hub 42 does not draw back in a sudden but draws back slowly against the frictional resistance between the bracing claw 242 and the inner wall of the push tube 21.

Figure 20:
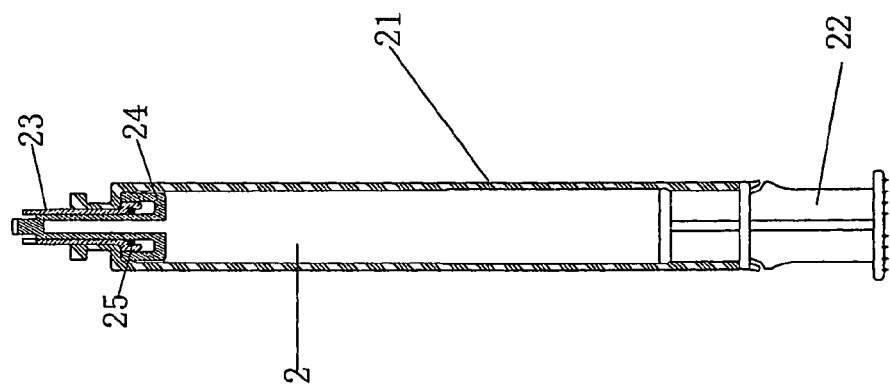
FIG. 20 is the cutaway view of the plunger.

The following is further detailed illustration in combination with each figure:

It is showed in FIG. 20 that the plunger 2 consists of a push tube 21, a handle 22 and a backup washer 23, a slow retraction bracket 24 and an airproof rubber ring 25.

Figure 18:
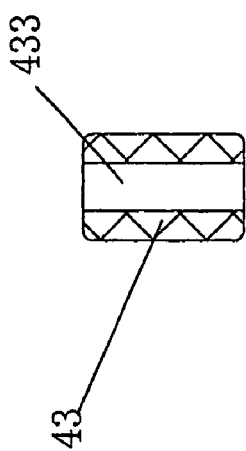
FIG. 18 is the cutaway view of the inner backing pin.
Figure 21:
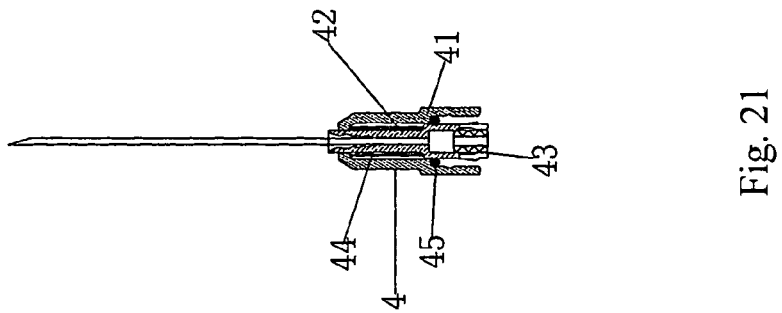
FIG. 21 is the cutaway view of the hub.

It is showed in FIG. 21 that the hub 4 consists of a hub sheath 41, an elastic connecting hub 42, an inner backing pin 43, a spring 44 and a rubber sealing ring 45. A thru slot 433 is provided at the middle part inside the backing pin 43 (see FIG. 18). A protection sheath 5 is installed outside the hub 4.

Figure 19:
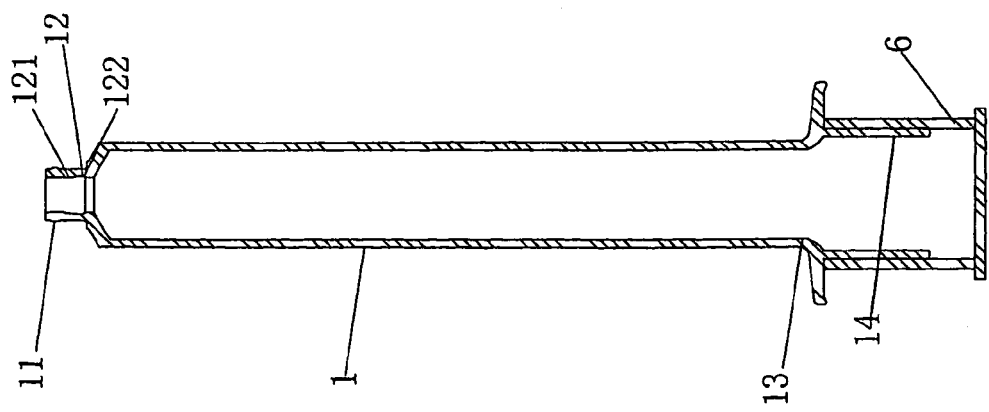
FIG. 19 is the cutaway view of the barrel.

It is showed in FIG. 19 that there is a boss 11 outside the head of the barrel 1. An inner pocket 12 is inside the head. A circle 14 is provided at the bottom. A big protection sheath 6 is provided outside the circle 14 to avoid wrong operation. An inner boss 13 is provided at the bottom of the barrel 1.

Figure 10:
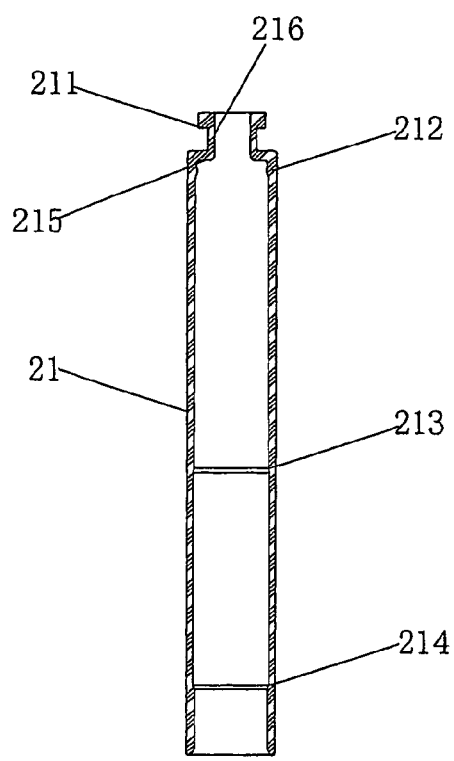
FIG. 10 is the cutaway view of the push tube.

It is showed in FIG. 10 that the push tube 21 is a hollow tube. A boss 211 is provided outside the top of it. There is a top surface 215 inside the tube. An inner boss 212 is provided inside the upper part. A step 213 is provided inside the middle part. The step 213 is inclined or straight. The step 213 is set in the middle part of the push tube 21 to enlarge the inner diameter of the push tube 21. An inclined step boss 214 is provided at the bottom inside push tube 21.

Figure 11:
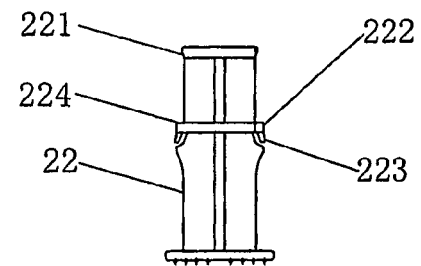
FIG. 11 is the cutaway view of the handle.

It is showed in FIG. 11 that boss 221 on the upper part of handle 22 closely joints with the inclined step boss 214 by clips at the bottom inside the push tube 21. At the middle part, there is a boss 222. The boss surface 224 touches the bottom of the push tube 21. More than two clips 223 are symmetrically set at the bottom. After injection, it joints with the boss 13 at the bottom of the barrel 1 by clips.

It is showed in FIG. 12 that there is a nick slot 231 on the head of the backup washer 23 and a protruding circle 236 at the bottom. The outside of the upper part is closely jointed with the piston 3. The outside of the middle part fits the inner hole 216 of the push tube 21 movably. At the bottom, there is an upper surface 232 of the boss jointing with the top surface 215 inside the push tube 21. At the bottom, an inner pocket 233 jointing with a rubber sealing ring 25 is provided. The outside of the protruding circle 236 at the bottom joints with the inner boss 2422 of the elastic bracing claw 242 of the slow retraction bracket 24.

It is showed in FIG. 13 that a thru slot 241 is provided on the top of the slow retraction bracket 24. Slow retraction bracket 24 joints with backup washer 23 and fits it movably. More than two elastic bracing claws 242 are provided outside the bottom of it. On the head of it, an outer boss 2421 superposes with the upper boss 212 inside the push tube 21. At this time, the boss 212 fastens and locates the elastic bracing claw 242. The inner boss 2422 joints with the outside of the protruding circle 236 at the bottom of the backup washer 23.

It is showed in FIG. 15 that the top surface 411 is set inside the hub sheath 41 touching the upper surface of spring 44. A middle boss surface 412 closely jointing with the rubber sealing ring 45 is provided in the middle part. A pocket 413 is provided at the middle bottom part inside, closely cooperating with the outer boss 11 of the head of the barrel 1.

Figure 16:
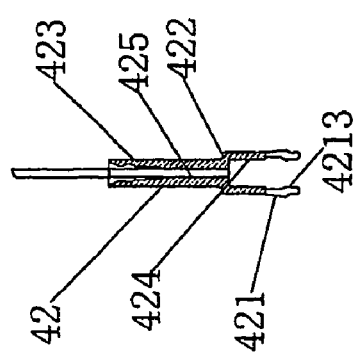
FIG. 16 is the cutaway view of the elastic connecting hub.

It is showed in FIG. 16 that at the bottom of the elastic connecting hub 42; more than two elastic bracing claws 242 are set symmetrically. The outer shapes of them correspond with the inner pocket 12 of the head of barrel 1 and closely joint with it by clips. The inner part 4213 of the elastic bracing claw 421 and the lower inside hole 424 joint with the outer wall of the inner backing pin 43. A step boss 422 is set in the middle of the elastic connecting hub 42, superposing with the bottom of the spring 44. The outer circle 423 of the elastic connecting hub 42 fits the inner hole of spring 44 movably. The upper inner hole 425 of the elastic connecting hub 42 cooperates with the injection needle.

Figure 2:
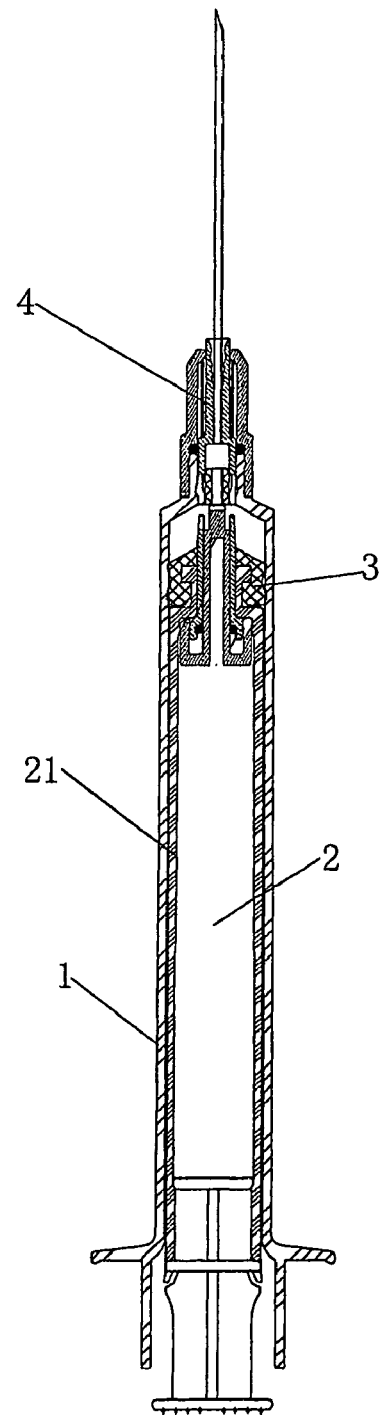
FIG. 2 is the cutaway view in the state of this invention preparing to draw liquid.
Figures 3, 4:
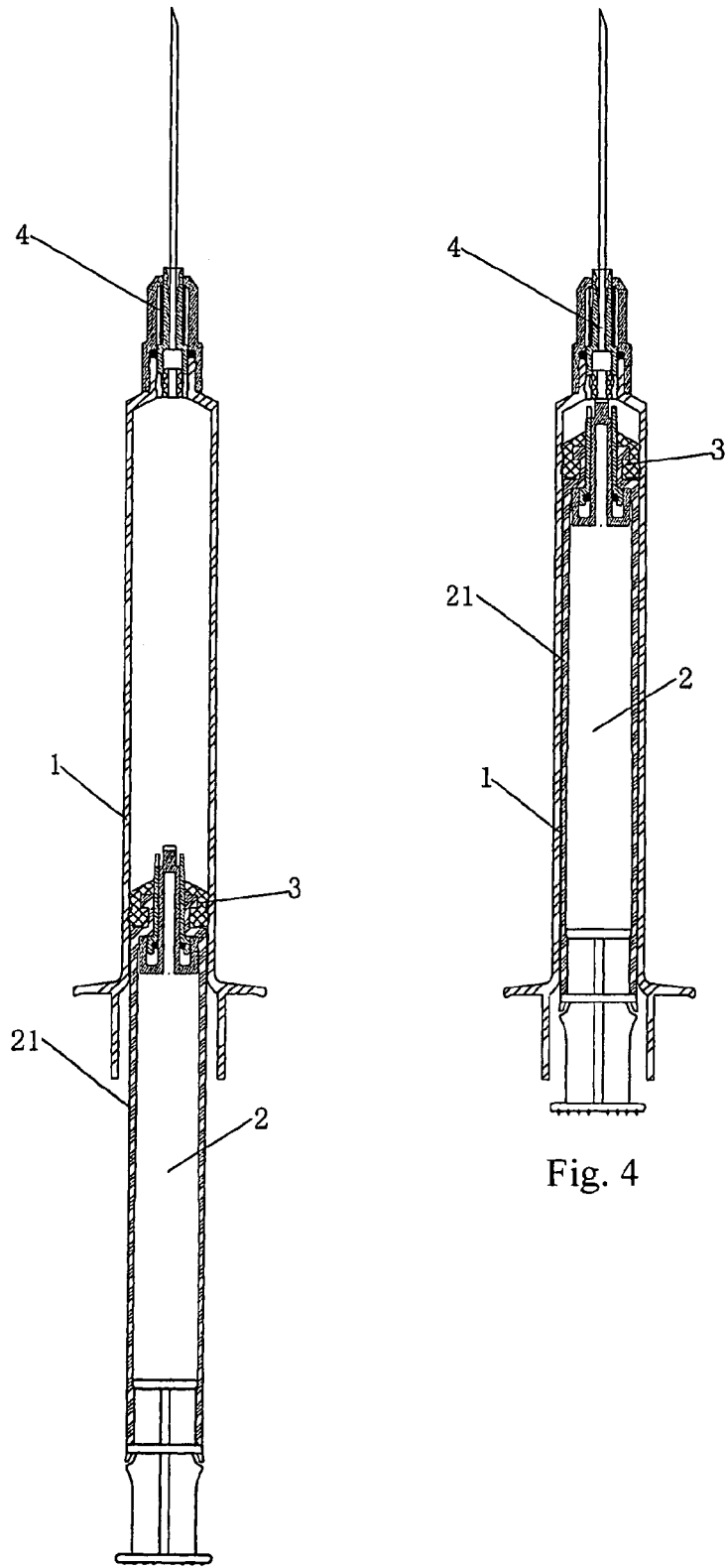
FIG. 3 is the cutaway view in the state of this invention having finished drawing liquid.
FIG. 4 is the cutaway view in the state of this invention having not pushed the liquid to the bottom and beginning to draw back and destroy itself
Figure 5:
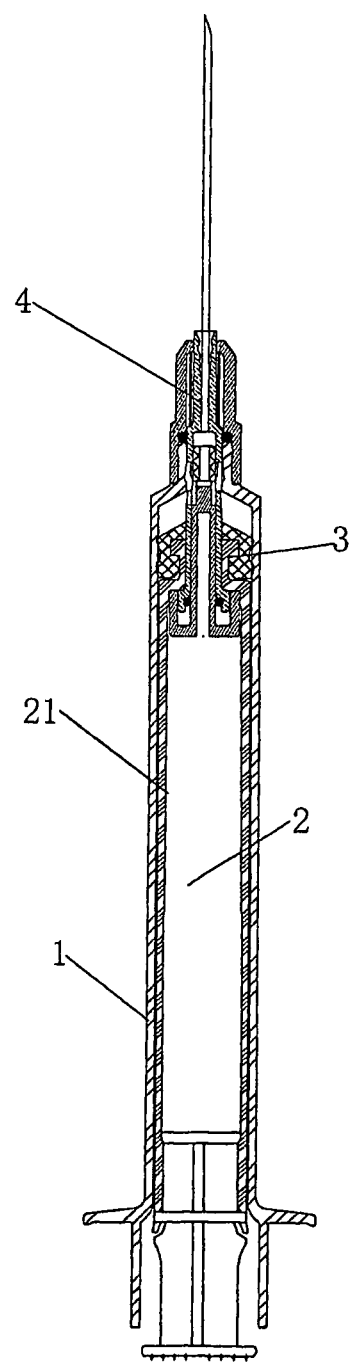
FIG. 5 is the cutaway view in the state of the end of the first step of the needle of this invention drawing back and destroying itself.
Figure 6:
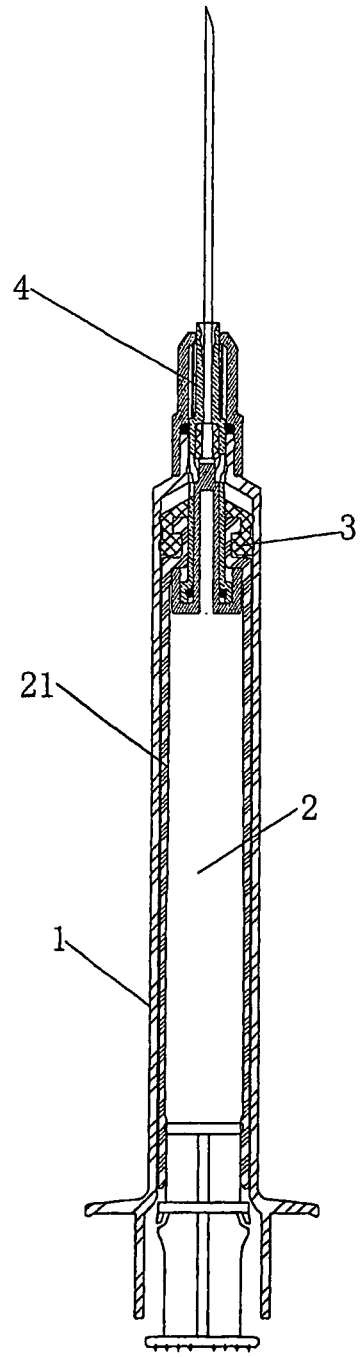
FIG. 6 is the cutaway view in the state of the end of the second step of the needle of this invention drawing back and destroying itself.
Figure 7:
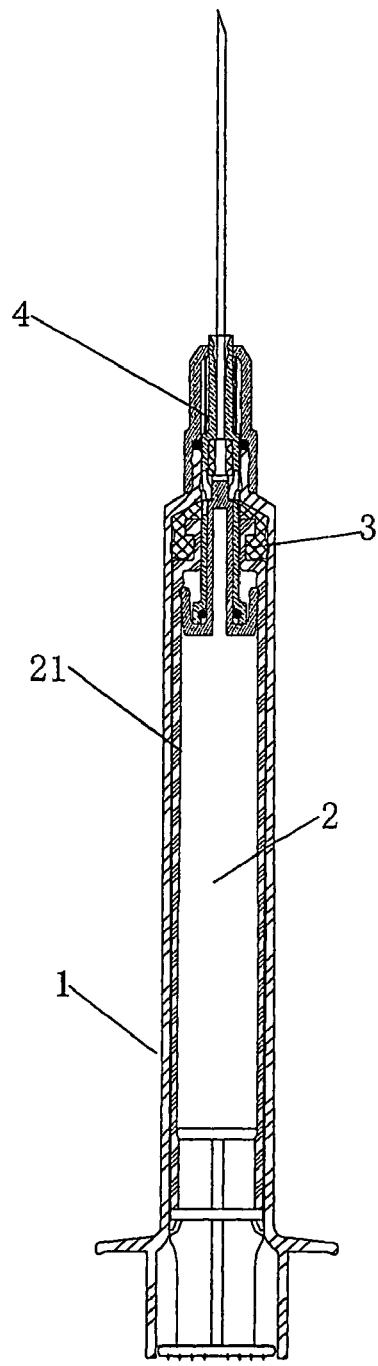
FIG. 7 is the cutaway view in the state of the end of the third step of the needle of this invention destroying itself and the end of injection, the needle beginning to draw back.
Figure 8:
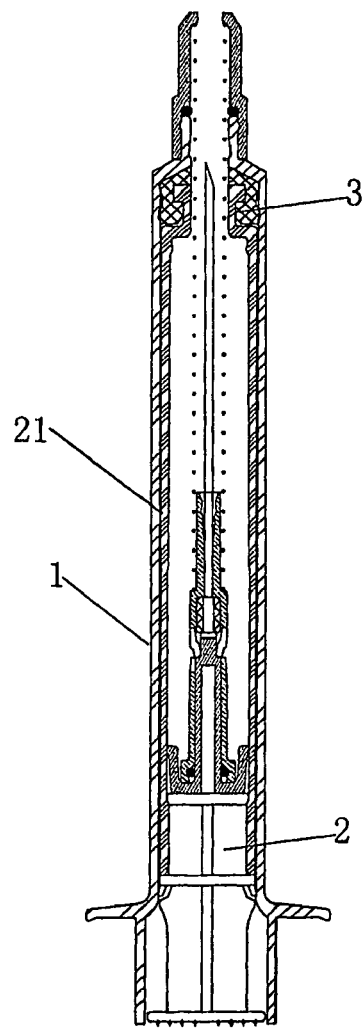
FIG. 8 is the cutaway view in the state of the needle of this invention drawing back into the barrel.
Figure 17:
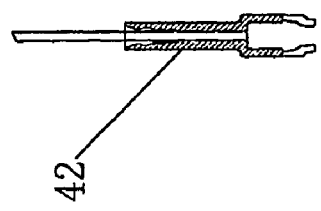
FIG. 17 is the cutaway view of transfigured elastic connecting hub.

FIGS. 1, 2, 3, 4, 5, 6, 7 and 8 show the whole process of using this invention. FIG. 1 shows the cutaway view in the state before use. At this time, the elastic bracing claw 242 on the slow retraction bracket 24 is fastened and located by an inner boss 212 of upper part inside the push tube 21. FIG. 2 is the cutaway view of preparing to draw liquid. At this time, the outside sheath 5 of the hub 4 and the big sheath 6 at the bottom of the barrel have been taken off. FIG. 3 is the cutaway view after finishing drawing liquid. FIG. 4 is the cutaway view in the state of liquid not being pushed to the bottom and drawing back and self destroying having started. The top of the slow retraction bracket 24 just touches the bottom of the inner backing pin 43. Liquid can flow through the thru slot 241 on the head of the slow retraction bracket 24. FIG. 5 is the cutaway view of the state at the end of the first step of the needle drawing back and destroying itself. At this time, the backing pin 43 is pushed into half of the hollow space of the elastic connecting hub 42 by the slow retraction bracket 24. The top of the backup washer 23 touches the bottom of the elastic bracing claw 421 on the elastic connective hub 42, preparing for the next action. FIG. 6 is the cutaway view in the state at the end of the second step of the needle drawing back and destroying itself. When the liquid is pushed forward, the slow retraction bracket 24 is pushed forward again because of movable fit between the backup washer 23 and the slow retraction bracket 24. At this time, the bottom of the backup washer 23 has relatively moved to the inner root part of the elastic bracing claw 242 of slow retraction bracket 24, which makes inner part of the head of the elastic bracing claw 242 lose support. Meanwhile, the inner backing pin 43 has been totally pushed into the elastic connecting hub 42. The elastic bracing claw 421 loses support and transfigures towards inside. FIG. 17 shows the transfiguration. Therefore, the elastic bracing claw 421 breaks away from the pocket 12 which cooperates with the head of barrel 1 and the elastic bracing claw 421 takes hold of the head of the slow retraction bracket 24, getting ready for drawing back the needle. FIG. 7 is the cutaway view in the state of the end of the third step of the needle drawing back and destroying itself after injection and beginning to draw back. When the liquid is pushed forward, inner part of the head of the elastic bracing claw 242 of the slow retraction bracket 24 is squeezed because of losing support and breaks away from the upper boss 212 inside the push tube 2. Later on, the elastic bracing claw 242 of the slow retraction bracket 24 transfigures through self springing, which is showed in FIG. 14, and touches the inner wall of the push tube 21. Liquid pushing is finished and drawing back starts. FIG. 8 is the cutaway view in the state of the needle drawing back into the push tube 21. When liquid pushing finishes, the elastic connecting hub 42 springs the slow retraction bracket 24 and the backup washer 23 under the springing force of the spring 44, which makes the elastic bracing claw 242 of the slow retraction bracket 24 slide down back to the push tube 21 along the inner wall of the push tube 21. At this time, because the elastic bracing claw 242 of the slow retraction bracket 24 has been transfigured and the elastic bracing claw 242 opposes to cooperate with the inner wall of the push tube 21, the elastic connecting hub 42 does not draw back in a sudden but slowly draws back against the frictional resistance between the elastic bracing claw 242 and the push tube 21. When the elastic bracing claw 242 goes down and slips to the middle part of the push tube 21, the inner diameter of the push tube 21 will become bigger due to a step set in the middle of the push tube, which reduces the resistance against the inner wall of the push tube 21 from the elastic bracing claw 242. Therefore, the frictional resistance between the elastic bracing claw 242 and the inner wall of the push tube 21 becomes less, cooperating with declining force of the spring, makes the elastic connecting hub 42 draw back and destroy itself successfully.

The above example is only to illustrate this invention and does not limit this invention. Ordinary technicians of related technical field can make more changes and transfiguration without breaking away from the spirit and scope of this invention. Therefore, all equivalent technical schemes belong to the scope of this invention.

The invention claimed is:

1. A safe medical syringe with an automatic slowly retractable needle, comprising:
   a hollow barrel;
   a plunger installed inside the hollow barrel, the plunger comprising a push tube and a rubber plunger on a distal end of the push tube;
   a hub provided on a distal end of the barrel, the hub a comprising (1) an elastic connecting hub portion that is retractable into the push tube and that houses an end of an injection needle and (2) a hub sheath surrounding the elastic connecting hub portion;
   a spring set disposed between the elastic connecting hub portion and the hub sheath, and providing a springing force in an axial direction between the hub sheath and the elastic connecting hub portion, the elastic connecting hub portion breaking away from the distal end of the barrel after injection and drawing back into the push tube by the springing force of the spring on the elastic connecting hub portion; and
   a slow retraction device cooperating with, and corresponding to a longitudinal axis of, the elastic connecting hub portion, the slow retraction device comprising (1) a backup washer and a slow retraction bracket joined together to form the slow retraction device, and (2) at least two elastic bracing claws that press outwardly and slidably interact with an inner wall of the push tube creating a frictional resistance against the inner wall of the push tube to slow the retraction of the slow retraction device.

2. The safe medical syringe as claimed in claim 1, further comprising:
   a thru slot on a distal end of the slow retraction bracket;
   an outer boss provided on each elastic bracing claw; and
   a first inner boss on the distal end of the push tube that engages the outer boss of each elastic bracing claw.

3. The safe medical syringe as claimed in claim 2, further comprising:
   a nick slot on a distal end of the backup washer;
   a protruding circle at a proximal end of the backup washer; and
   a second inner boss on each elastic bracing claw,
   wherein an outside of the protruding circle joins with the second inner boss of each elastic bracing claw.

4. The safe medical syringe as claimed in claim 3 wherein:
   an outside of an axially center portion of the backup washer closely cooperates movably with the rubber plunger and an inner hole on the distal end of the push tube;
   a portion of the protruding circle joins a surface adjacent to the inner hole; and
   an inner pocket inside the protruding circle joins with an airproof rubber sealing ring.

5. The safe medical syringe as claimed in claim 1, further comprising:
   an inner pocket within a hole on the distal end of the hollow barrel;
   at least two elastic connecting huh bracing claws provided at the proximal end of the elastic connecting hub, the at least two elastic connecting hub bracing claws being symmetrically positioned to correspond to a shape of the inner pocket within the hole on the distal end of the hollow barrel such that the at least two elastic connecting hub bracing claws engage with the inner pocket; and
   an inner backing pin set as support in a hollow space between the at least two elastic connecting hub bracing claws.

6. The safe medical syringe as claimed in claim 1, further comprising:
   a boss outside of a hole on the distal end of the hollow barrel;
   a first surface inside a hole on the distal end of the hub sheath that contacts a distal end of the spring;
   a second surface on an inside of a step between ends of the hub sheath that receives an airproof rubber sealing ring that creates a seal between the hub sheath, the elastic connecting hub portion and the distal end of the hollow barrel; and a pocket inside the proximal end of the hub sheath that joins with the boss outside of the hole on the distal end of the hollow barrel.

7. The safe medical syringe as claimed in claim 1, further comprising:
- a step on the outside of the elastic connecting hub portion between ends of the elastic connecting hub portion, wherein a proximal end of the spring contacts the step;
- an outer circle on a distal end of the elastic connecting hub portion fits movably within a first inner hole of the spring; and
- a second inner hole inside the distal end of the elastic connecting hub portion houses an end of the injection needle.

8. The safe medical syringe as claimed in claim 1, further comprising:
- an inner boss on an inside of the proximal end of the hollow barrel;
- an inclined inner step boss on an inside of the proximal end of the push tube;
- a handle at a proximal end of the push tube;
- a first protrusion on a distal end of the handle that engages with the inclined inner step boss on the inside of the proximal end of the push tube;
- a second protrusion in an axially middle portion of the handle that joins with the proximal end of the push tube; and
- at least two clips symmetrically located adjacent to the second protrusion that join the push tube with the hollow barrel by clipping with the inner boss after injection.

9. The safe medical syringe as claimed in claim 1, further comprising:
- a circle on a proximal end of the hollow barrel;
- a handle protection sheath installed outside the circle; and
- a needle protection sheath installed outside the hub.

10. The safe medical syringe as claimed in claim 2, further comprising:
- an inner pocket within a hole on the distal end of the hollow barrel;
- at least two elastic connecting hub bracing claws provided at the proximal end of the elastic connecting hub, the at least two elastic connecting hub bracing claws being symmetrically positioned to correspond to a shape of the inner pocket within the hole on the distal end of the hollow barrel such that the at least two elastic connecting hub bracing claws engage with the inner pocket; and
- an inner backing pin set as support in a hollow space between the at least two elastic connecting hub bracing claws.

11. The safe medical syringe as claimed in claim 3, further comprising:
- an inner pocket within a hole on the distal end of the hollow barrel;
- at least two elastic connecting hub bracing claws provided at the proximal end of the elastic connecting hub, the at least two elastic connecting hub bracing claws being symmetrically positioned to correspond to a shape of the inner pocket within the hole on the distal end of the hollow barrel such that the at least two elastic connecting hub bracing claws engage with the inner pocket; and
- an inner backing pin set as support in a hollow space between the at least two elastic connecting hub bracing claws.

12. The safe medical syringe as claimed in claim 4, further comprising:
- a second inner pocket within a hole on the distal end of the hollow barrel;
- at least two elastic connecting hub bracing claws provided at the proximal end of the elastic connecting hub, the at least two elastic connecting hub bracing claws being symmetrically positioned to correspond to a shape of the second inner pocket within the hole on the distal end of the hollow barrel such that the at least two elastic connecting hub bracing claws engage with the second inner pocket; and
- an inner backing pin set as support in a hollow space between the at least two elastic connecting huh bracing claws.

13. The safe medical syringe as claimed in claim 2, further comprising:
- a boss outside of a hole on the distal end of the hollow barrel;
- a first surface inside a hole on the distal end of the hub sheath that contacts a distal end of the spring;
- a second surface on an inside of a step between ends of the hub sheath that receives an airproof rubber sealing ring that creates a seal between the hub sheath, the elastic connecting hub portion and the distal end of the hollow barrel; and
- a pocket inside the proximal end of the hub sheath that joins with the outside of the hole on the distal end of the hollow barrel.

14. The safe medical syringe as claimed in claim 3, further comprising:
- a boss outside of a hole on the distal end of the hollow barrel;
- a first surface inside a hole on the distal end of the hub sheath that contacts a distal end of the spring;
- a second surface on an inside of a step between ends of the hub sheath that receives an airproof rubber sealing ring that creates a seal between the hub sheath, the elastic connecting hub portion and the distal end of the hollow barrel; and
- a pocket inside the proximal end of the hub sheath that joins with the boss outside of the hole on the distal end of the hollow barrel.

15. The safe medical syringe as claimed in claim 4, further comprising:
- a boss outside of a hole on the distal end of the hollow barrel;
- a first surface inside a hole on the distal end of the hub sheath that contacts a distal end of the spring;
- a second surface on an inside of a step between ends of the hub sheath that receives an airproof rubber sealing ring that creates a seal between the hub sheath, the elastic connecting hub portion and the distal end of the hollow barrel; and
- a pocket inside the proximal end of the hub sheath that joins with the boss outside of the hole on the distal end of the hollow barrel.

16. The safe medical syringe as claimed in claim 2, further comprising:
- a step on the outside of the elastic connecting hub portion between ends of the elastic connecting hub portion, wherein a proximal end of the spring contacts the step;
- an outer circle on a distal end of the elastic connecting hub portion fits movably within a first inner hole of the spring; and
- a second inner hole inside the distal end of the elastic connecting hub portion houses an end of the injection needle.

17. The safe medical syringe as claimed in claim 3, further comprising:

a step on the outside of the elastic connecting hub portion between ends of the elastic connecting hub portion, wherein a proximal end of the spring contacts the step;

an outer circle on a distal end of the elastic connecting hub portion fits movably within a first inner hole of the spring; and a second inner hole inside the distal end of the elastic connecting hub portion houses an end of the injection needle.

18. The safe medical syringe as claimed in claim 4, further comprising:

a step on the outside of the elastic connecting hub portion between ends of the elastic connecting hub portion, wherein a proximal end of the spring contacts the step;

an outer circle on a distal end of the elastic connecting hub portion fits movably within a second inner hole of the spring; and a third inner hole inside the distal end of the elastic connecting hub portion houses an end of the injection needle.

19. The safe medical syringe as claimed in claim 2, further comprising:

a second inner boss on an inside of the proximal end of the hollow barrel;

an inclined inner step boss on an inside of the proximal end of the push tube;

a handle at the bottom at a proximal end of the push tube;

a first protrusion on a distal end of the handle that engages with the inclined inner step boss on the inside of the proximal end of the push tube;

a second protrusion in an axially middle portion of the handle that joins with the proximal end of the push tube; and at least two clips symmetrically located adjacent to the second protrusion that join the push tube with the hollow barrel by clipping with the second inner boss after injection.

20. The safe medical syringe as claimed in claim 3, further comprising:

a third inner boss on an inside of the proximal end of the hollow barrel;

an inclined inner step boss on an inside of the proximal end of the push tube;

a handle at a proximal end of the push tube;

a first protrusion on a distal end of the handle that engages with the inclined inner step boss on the inside of the proximal end of the push tube;

a second protrusion in an axially middle portion of the handle that joins with the proximal end of the push tube; and at least two clips symmetrically located adjacent to the second protrusion that loin the push tube with the hollow barrel by clipping with the third inner boss after injection.

21. The safe medical syringe as claimed in claim 4, further comprising:

a third inner boss on an inside of the proximal end of the hollow barrel;

an inclined inner step boss on an inside of the proximal end of the push tube;

a handle at a proximal end of the push tube;

a first protrusion on a distal end of the handle that engages with the inclined inner step boss on the inside of the proximal end of the push tube;

a second protrusion in an axially middle portion of the handle that joins with the proximal end of the push tube; and at least two clips symmetrically located adjacent to the second protrusion that join the push tube with the hollow barrel by clipping with the third inner boss after injection.

22. The safe medical syringe as claimed in claim 2, further comprising:

a circle on a proximal end of the hollow barrel;

a handle protection sheath installed outside the circle; and a needle protection sheath installed outside the hub.

23. The safe medical syringe as claimed in claim 3, further comprising:

a second circle on a proximal end of the hollow barrel;

a handle protection sheath installed outside the second circle; and a needle protection sheath installed outside the hub.

24. The safe medical syringe as claimed in claim 4, further comprising:

a second circle on a proximal end of the hollow barrel;

a handle protection sheath installed outside the circle; and a needle protection sheath installed outside the hub.

* * * * *

UNITED STATES PATENT AND TRADEMARK OFFICE
CERTIFICATE OF CORRECTION

PATENT NO. : 7,993,307 B2
APPLICATION NO. : 12/225820
DATED : August 9, 2011
INVENTOR(S) : Zuoqian Lin Page 1 of 1

It is certified that error appears in the above-identified patent and that said Letters Patent is hereby corrected as shown below:

Title Page,

Please add Item (30) Foreign Application Priority Data

--April 13, 2006 (CN) 200610050366.5--

Signed and Sealed this
Twenty-fifth Day of September, 2012

David J. Kappos
*Director of the United States Patent and Trademark Office*